(12) United States Patent
Huang et al.

(10) Patent No.: US 11,491,486 B2
(45) Date of Patent: Nov. 8, 2022

(54) SYSTEMS, METHODS, AND STRUCTURES FOR SURFACE ACOUSTIC WAVE-BASED SEPARATION

(71) Applicant: Duke University, Durham, NC (US)

(72) Inventors: Jun Huang, Durham, NC (US); Mengxi Wu, Durham, NC (US)

(73) Assignee: Duke University, Durham, NC (US)

( * ) Notice: Subject to any disclaimer, the term of this patent is extended or adjusted under 35 U.S.C. 154(b) by 234 days.

(21) Appl. No.: 16/642,641

(22) PCT Filed: Aug. 29, 2018

(86) PCT No.: PCT/US2018/048629
§ 371 (c)(1),
(2) Date: Feb. 27, 2020

(87) PCT Pub. No.: WO2019/046483
PCT Pub. Date: Mar. 7, 2019

(65) Prior Publication Data
US 2021/0154668 A1    May 27, 2021

Related U.S. Application Data

(60) Provisional application No. 62/551,270, filed on Aug. 29, 2017.

(51) Int. Cl.
*B01L 3/00* (2006.01)
*G01N 29/22* (2006.01)

(52) U.S. Cl.
CPC ...... *B01L 3/502753* (2013.01); *G01N 29/222* (2013.01); *B01L 2400/0436* (2013.01); *G01N 2291/0423* (2013.01)

(58) Field of Classification Search
None
See application file for complete search history.

(56) References Cited

U.S. PATENT DOCUMENTS

| 2003/0150806 A1 | 8/2003 | Hobbs et al. |
| 2010/0139377 A1 | 6/2010 | Huang et al. |

(Continued)

FOREIGN PATENT DOCUMENTS

WO    2016/025518 A1    2/2016

OTHER PUBLICATIONS

Lee et al., Acoustic Purification of Extracellular Microvesicles, 2015, ACS Nano., 9(3), p. 1-14 (or p. 2321-2327). (Year: 2015).*

(Continued)

*Primary Examiner* — Lore R Jarrett
(74) *Attorney, Agent, or Firm* — Kaplan Breyer Schwarz, LLP

(57) ABSTRACT

Aspects of the present disclosure describe systems, methods, and structures for acoustic wave-based separation of particulates in a fluidic flow. Illustrative systems, methods, and structures according to aspects of the present disclosure may advantageously provide for the continuous, label-free, non-invasive separation of the particulates that include—among other types—difficult-to-separate biological particulates and in particular those in blood including circulating tumor cells and micro-blood-borne particles and other subgroups of extracellular vesicles including nanoscale exosomes.

7 Claims, 12 Drawing Sheets

(56) References Cited

U.S. PATENT DOCUMENTS

| | | | |
|---|---|---|---|
| 2011/0154890 A1 | 6/2011 | Holm et al. | |
| 2014/0033808 A1* | 2/2014 | Ding | C12M 47/04 73/61.75 |
| 2016/0139012 A1* | 5/2016 | D'Silva | B01L 3/502753 435/6.1 |

OTHER PUBLICATIONS

Authorized Officer: Blaine R. Copenheaver, International Search Report and Written Opinion issued in counterpart PCT application No. PCT/US2018/048629, dated Dec. 27, 2018, 12 pp.

* cited by examiner

SYSTEMS, METHODS, AND STRUCTURES FOR SURFACE ACOUSTIC WAVE-BASED SEPARATION

CROSS REFERENCE TO RELATED APPLICATION

This application claims the benefit of Untied States Provisional Patent Application Ser. No. 62/551,270 filed 29 Aug. 2017 the entire content of which is incorporated by reference as if set forth at length herein.

STATEMENT OF GOVERNMENTAL INTEREST

This disclosure describes an invention made with United States Government support under Federal Grant Nos. R01HD086325 and IIP-1534645 awarded by the National Institute of Health (NIH) and National Science Foundation (NSF), respectively. The United States Government has certain rights in this invention.

TECHNICAL FIELD

This disclosure relates generally to separation science. More particularly, it pertains to systems, methods, and structures that employ surface acoustic waves (SAWs) to manipulate objects in fluid(s). Such systems, methods, and structures find applicability in processing complex biological samples—including blood—and in on illustrative application may advantageously provide for the detection of circulating tumor cells in a subject and/or the separation/isolation of exosomes.

BACKGROUND

The ability to separate particulate components in complex biological fluidic samples is of increasing importance in several areas of disease research including cancer. At the cellular level, circulating tumor cells (CTCs) have been extensively investigated and preliminary studies have inspired the belief that CTCs can be employed as a minimally invasive window—a so-called "liquid biopsy"—to provide valuable guidance for cancer therapy. Similarly, researchers have learned that exosomes—nanoscale extracellular vesicles that perform diverse cellular functions including intercellular communications, antigen presentation and the transfer of proteins, mRNA and MiRNA—are related to the pathogenesis of various diseases.

A complete understanding of the relationship(s) between such particulate components in complex biological fluidic samples has not been fully realized—in part—due to the inability to collect and subsequently separate and/or isolate these components in a rapid, biocompatible, and highly accurate way. Consequently, systems, methods, and structures that provide for such separation would represent a welcome addition to the art.

SUMMARY

An advance in the art is made according to aspects of the present disclosure directed to systems, methods, and structures for the separation of particulate components of complex biological fluidic samples in a label-free, contactless, continuous, high-throughput, biocompatible manner.

In sharp contrast to the prior art, an illustrative embodiment of the present disclosure provides a device that comprises a channel exhibiting a hybrid structure utilizing a soft polymer as a channel wall and a hard material (e.g., glass, silicon oxide, etc.) as a channel top. This hybrid channel advantageously enables the formation of a standing surface acoustic wave (SAW) field in fluid flowing in the channel while enhancing acoustic pressure through a vertical resonance effect.

Viewed from another illustrative embodiment, the present disclosure provides a unique channel divider feature that advantageously creates extra boundary layers in the fluid domain flowing therein. Consequently, fluid flowing in the channel exhibits a desirable velocity profile that advantageously increase(s) lateral shifts of particles in the SAW field(s), thereby improving separation.

Viewed from still another illustrative embodiment, the present disclosure provides a device that includes two individual SAW-based separation units that are integrated into a single device. When the two SAW units exhibit different operational working characteristics such as frequency and/or input power, the may advantageously separate different subgroups of objects in a fluid containing a variety of particulate components. Such multi-separation-device integration and operation advantageously enables the ability to process more complex fluid samples, e.g., blood.

Viewed from still another illustrative aspect, the present disclosure enables application methods for separating/isolating—among other things—circulating tumor cells and/or exosomes in a biological sample.

BRIEF DESCRIPTION OF THE DRAWING

A more complete understanding of the present disclosure may be realized by reference to the accompanying drawing in which:

FIG. 4(D) top view of the velocity distributions in the conventional channel (top) and modified channel with a divider (bottom) wherein arrows indicate positions of particles flowing in either channel with perimeter regions exhibiting low velocity while central regions exhibiting higher velocities; FIG. 4(E) velocity distribution curves across the channels showing that in the modified channel a low velocity region was created in the center after the PDMS divider and the velocity profiles in planes at 0.5, 1.5, 2.5, and 35 mm, with respect to the flow direction, after the PDMS divider are graphed; and FIG. 4(F) experimental data showing the lateral deflection displacements of particles (CTCs, WBCs) impacted by velocity—wherein a slower velocity increased the displacement;

Figure 1A:
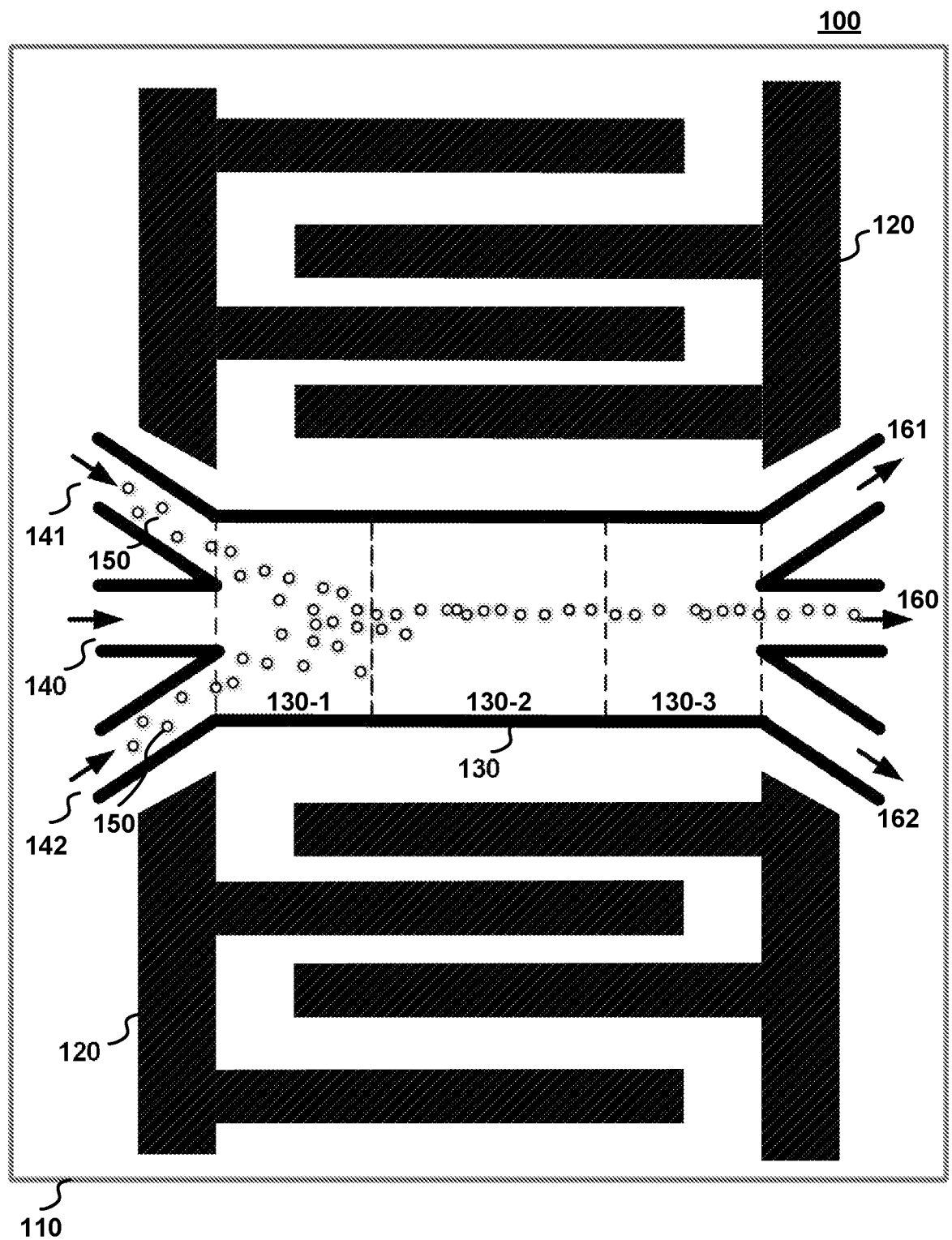
FIG. 1(A) is a schematic diagram of a prior art arrangement for particle separation using standing surface acoustic wave (SSAW)-induces acoustophoresis in a microfluidic channel.

The illustrative embodiments are described more fully by the Figures and detailed description. Embodiments according to this disclosure may, however, be embodied in various forms and are not limited to specific or illustrative embodiments described in the drawing and detailed description.

DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are intended to be only for pedagogical purposes to aid the reader in understanding the principles of the disclosure and the concepts contributed by the inventor(s) to furthering the art and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that any block diagrams herein represent conceptual views of illustrative circuitry embodying the principles of the disclosure.

Unless otherwise explicitly specified herein, the FIGs comprising the drawing are not drawn to scale.

By way of some additional background, we begin by noting that acoustic-based particle manipulation techniques have been proven to be quite useful for particle and cell manipulation(s), as numerous acousto-fluidic systems have been developed to separate and/or sort such particle and/or cells. Since these techniques exhibit non-contact and non-invasive characteristics, they have rapidly become key enablers of numerous biomedical applications.

One such technique employs standing surface acoustic wave(s) (SSAW) to manipulate particulate and/or cellular-scale objects. More particularly, standing SAW-induced acoustic radiation forces are used to change the physical location/orientation of the objects such that separation/sorting results. Of particular advantage, such techniques and systems constructed therefrom may be conveniently integrated with other devices employed in the biological, chemical, and physical sciences to perform versatile, low power, non-contact, non-invasive separation/sorting.

FIG. 1(A) is a top-view, schematic diagram of a prior art arrangement for particle separation using standing surface acoustic wave (SSAW)-induced acoustophoresis in a microfluidic channel 130. As may be observed from that figure, the microfluidic channel is shown integrated onto a single chip 110 which also includes a pair of interdigitated transducers 120 that are positioned on either side of the channel substantially along its entire length.

Operationally, the generalized structure shown provides continuous particle separation through the effect of standing surface acoustic wave (SSAW)-induced acoustophoresis in the microfluidic channel. As illustrated in the figure—using this SSAW-based method, particles 150 in a continuous laminar flow are separated based on their volume, density and compressibility.

With continued reference to FIG. 1, it may be observed that a mixture of particles—generally exhibiting an equal density but dissimilar volumes—is injected into a microchannel through two side inlets 141, 142, sandwiching a deionized water sheath flow injected through a central inlet 140. A one-dimensional SSAW generated by the two parallel interdigital transducers (IDTs) is established across the channel, with the channel spanning a single SSAW pressure node located at the channel center—depicted by region 130-2. Application of the SSAW induces larger axial acoustic forces on the particles of larger volume, repositioning them closer to the wave pressure node at the center of the channel. Accordingly, as particles undergo the laminar flow through regions 130-1, 130-2 and 130-3, the particles are laterally moved to different regions of the channel cross-section based on the particle volume. As shown in the figure, the particles injected into the two side inlets are gradually repositioned to a substantially central, axial region of the channel, and subsequently output port 160. As will be readily appreciated by those skilled in the art, such particle separation method is simple and versatile, capable of separating virtually all kinds of particles (regardless of charge/polarization or optical properties) with high separation efficiency and low power consumption.

Figure 1B:
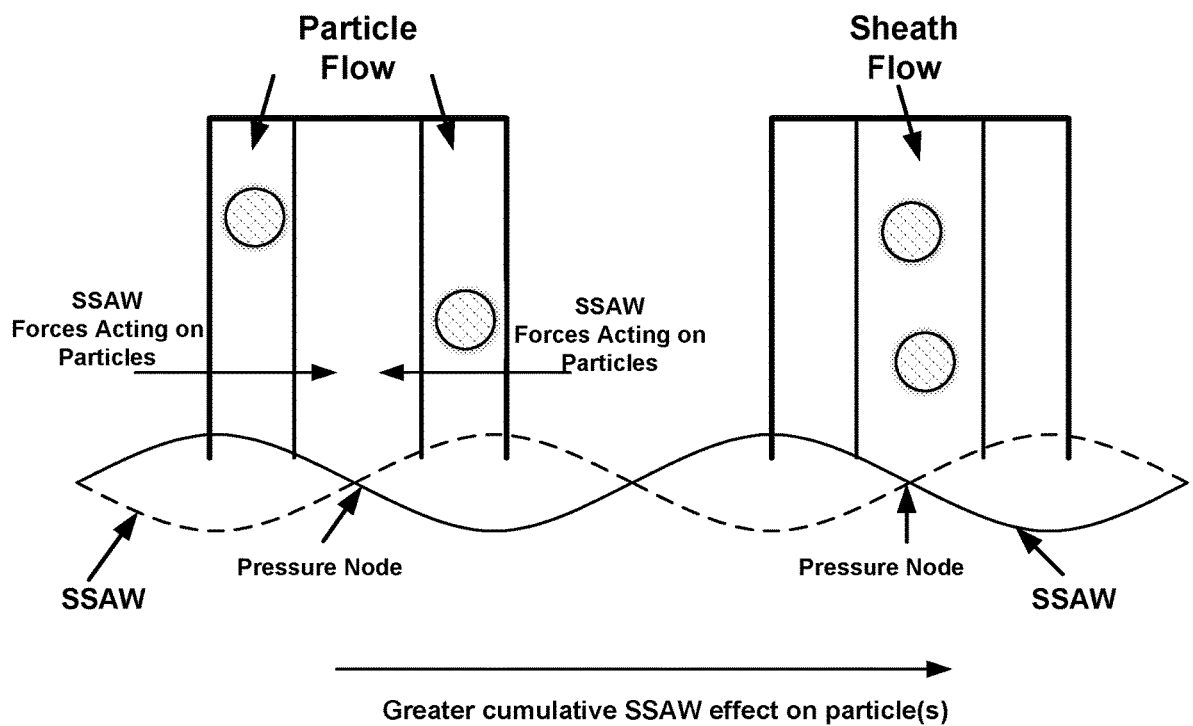
FIG. 1(B) is a schematic diagram of a cross-section of a microfluidic channel illustrating how SSAWs may be used to redirect particles undergoing separate particle flow into a unified sheath flow in a microfluidic channel structure.

FIG. 1(B) is a schematic diagram of a cross-section of a microfluidic channel illustrating how SSAWs may be used to redirect particles undergoing separate particle flow into a unified sheath flow in a microfluidic channel structure. As may be observed from that figure, left side, particles undergoing flow in the microfluidic channel experience SSAW forces acting on the particles. As illustrated, the SSAW forces acting on the particles induce a central migration of the particles—toward the pressure node of the SSAW. After undergoing such effect(s) for a length of the channel, the SSAW effect is cumulative and the particles may migrate into a "sheath" flow shown in the figure as being substantially centrally, axially located within the sheath of the overall laminar flow within the microfluidic channel.

As we shall show and describe in greater detail, such particle re-directing by an SSAW does not have to be centrally directed and may be directed to one side or another of the channel—as desired by application requirements.

Figure 2:
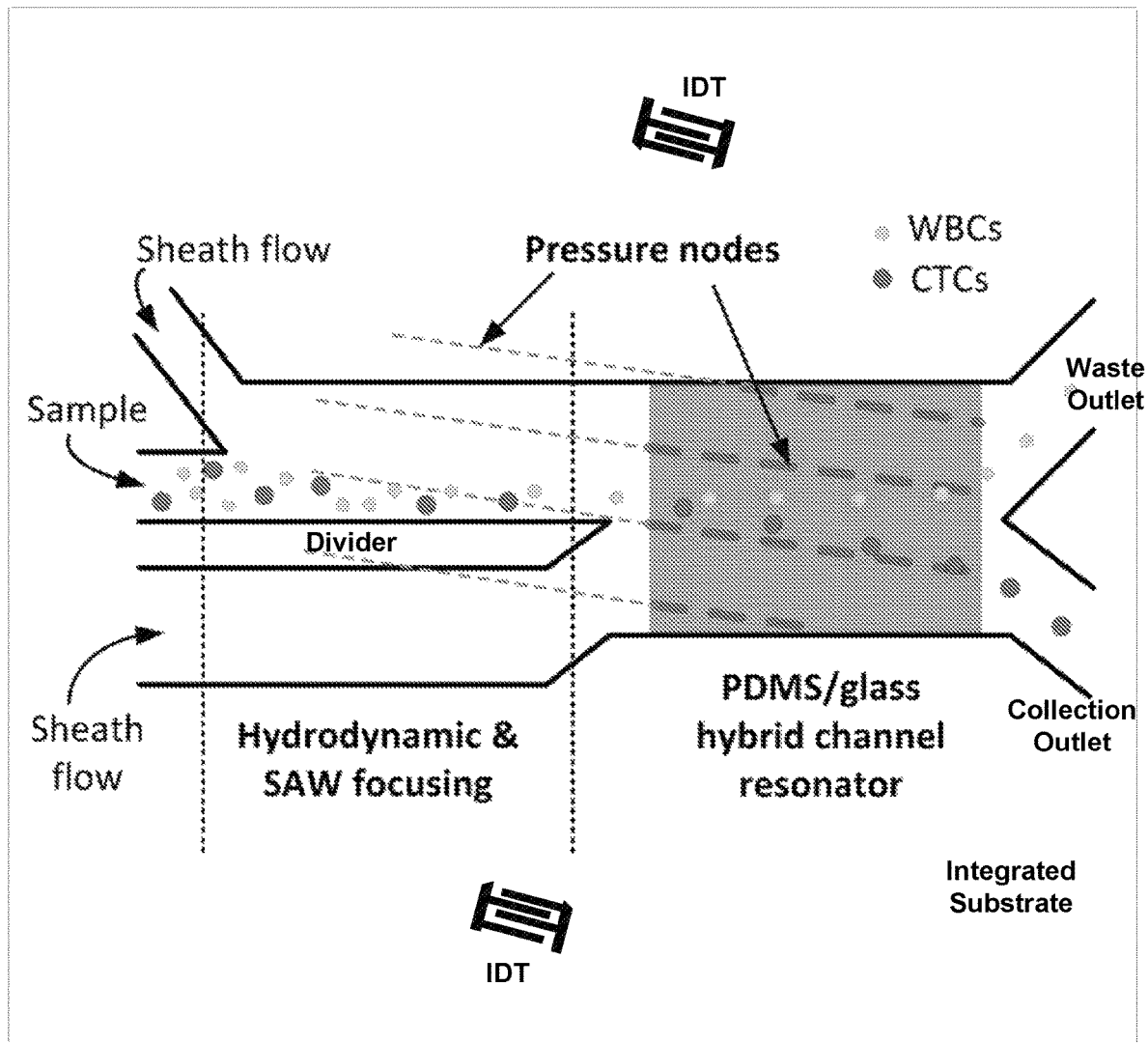
FIG. 2 is a schematic diagram top-view of an illustrative improved microfluidic channel employing tilted angle standing surface acoustic waves (taSSAW) to redirect particles undergoing particle flow in the channel according to aspects of the present disclosure.
Figure 3:
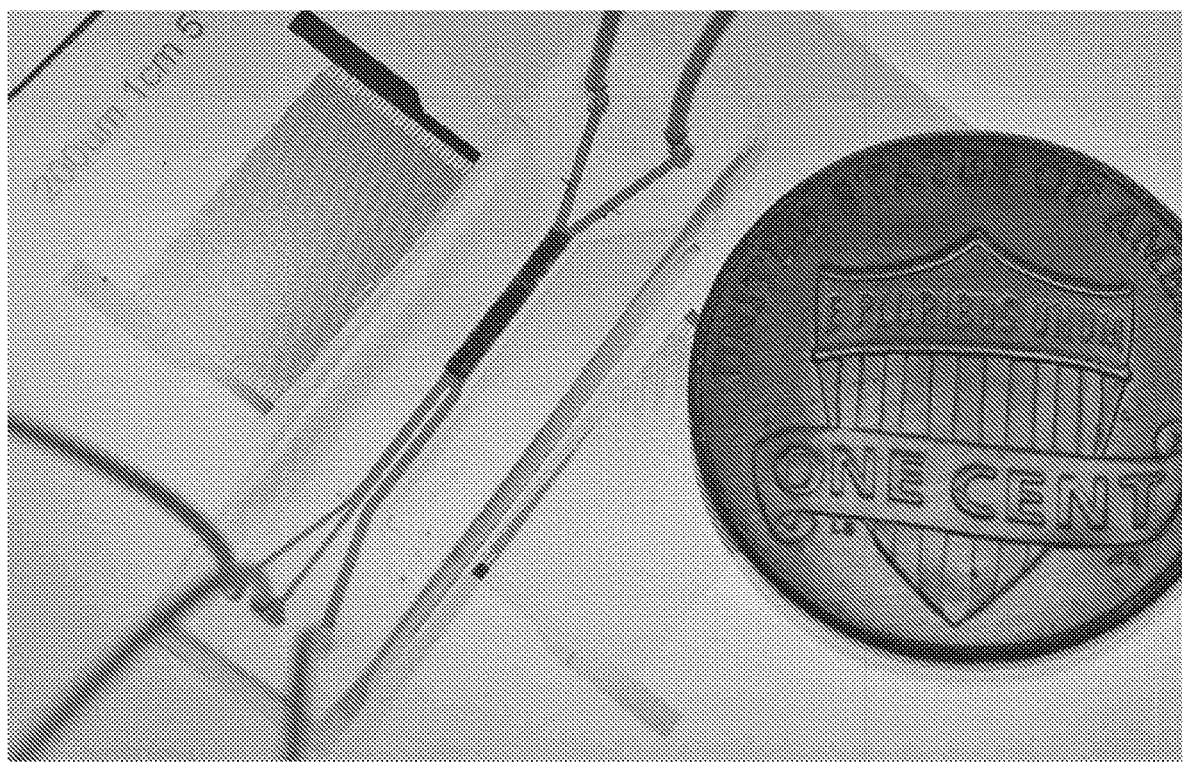
FIG. 3 is a photo-illustration of a microfluidic channel separation device employing ttSSAW according to aspects of the present disclosure.

FIG. 2 is a schematic diagram top-view of an illustrative improved microfluidic channel employing tilted angle standing surface acoustic waves (taSSAW) to redirect particles undergoing particle flow in the channel according to aspects of the present disclosure. FIG. 3 is a photo-illustration of a microfluidic channel separation device of FIG. 2 employing ttSSAW according to aspects of the present disclosure.

With reference now to that FIG. 2, we note that the structure shown therein generally includes a microfluidic channel having three inlet ports (one central sample port and two sheath flow ports—one on each side of the sample port)—and two outlet ports at an opposite end of the channel. Advantageously, the overall channel structure(s) may be formed on a single, integrated substrate. Shown further is a channel divider structure, positioned between the sample port and one of the sheath ports. As shown further and as will be described in operational detail, the length of the micro channel is defined by several regions including a hydrodynamic and SAW focusing region and a PDMS/glass hybrid channel resonator region.

As illustrated in FIG. 2, sample particles—in this illustrative example, larger, circulating tumor cells and smaller white blood cells—are injected into the central sample port while fluids are concurrently injected into the sheath flow ports. Cells are focused along the divider and in the hybrid PDMS-glass channel resonating region circulating tumor cells (larger particles) and white blood cells (smaller particles) are separated due to the difference(s) in lateral shift. Through the combined effects of the divider structure in the hydrodynamic and SAW focusing region and the applied ttSSAW effect(s) in the PDMS/glass hybrid channel resonator region, the particles are separated such that the white blood cells are directed to one of the two output ports (the upper one in this illustrative figure) while the circulating tumor cells are directed to the other output port (the lower one in this illustrative figure).

At this point we note that the improved structure shown schematically in FIG. 2 advantageously exhibits an improved throughput over prior art acoustic separation methods/structures by about seven-fold wile exhibiting a high-throughput that can process approximately 7.5 mL of a cell solution within an hour. As noted previously and shown illustratively in FIG. 2, the structures according to the present disclosure employ tilted angle standing acoustic waves (taSSAW)—which result in the diagonal pressure nodes shown in the figure.

To further improve the throughput, the device is advantageously constructed including a polydimethylsiloxane (PDMS) glass-hybrid channel to form an acoustic enclosure. Accordingly, acoustic wave(s) generated by piezoelectric substrate structures reflects into the channel and resonates, thereby increasing the energy density and resulting throughput.

In addition to the hybrid PDMS-glass channel, a "velocity shadow"—resulting from the divider structure—is provided in the structure. The velocity shadow causes a local decrease in particle velocity resulting in improved separation and specificity due to a longer resulting travel time of the particles within the acoustic field.

Note that the divider structure generates additional boundary layers in the fluid domain. Accordingly, fluid flowing through the overall structure will exhibit an advantageous velocity profile (i.e., "saddle shaped") while devices without the divider structure exhibit a more parabolic velocity profile. The specific velocity profile change increases the lateral shifts of particles in the SAW field, thereby improving separation efficiency.

As will be appreciated, along the additional boundary layer(s) formed by the divider in the microfluidic channel results in a slowing down of the particle movement in regions proximate to those boundaries. Consequently, the SAW has a prolonged action/effect on the slowed particles and greater lateral shift results.

With continued simultaneous reference to FIG. 2 and FIG. 3, we note that the illustrative acoustic separation structure includes the PDMS microfluidic channel bonded to a piezoelectric substrate between a pair of interdigitated transducers (IDTs). Operationally, when radio frequency voltage signals are applied to the IDTs, the IDTs generate two Rayleigh waves travelling in opposite directions which interfere within the microfluidic channel. Thus, a standing wave field is formed where periodic wave nodes and antinodes are generated. Cells flowing through these periodic pressure nodes and antinodes are subjected to different acoustic radiation forces, resulting in lateral displacement.

Note further that the acoustic radiation forces are linearly related to the acoustic energy density. To enhance the acoustic energy density within the microchannel and to improve the throughput of the acoustic separation device, we employed a PDMS-glass hybrid channel to form an acoustic enclosure. In particular, we embedded a thin glass layer (130 µm in thickness) at the top of the microchannel.

Figure 4A:
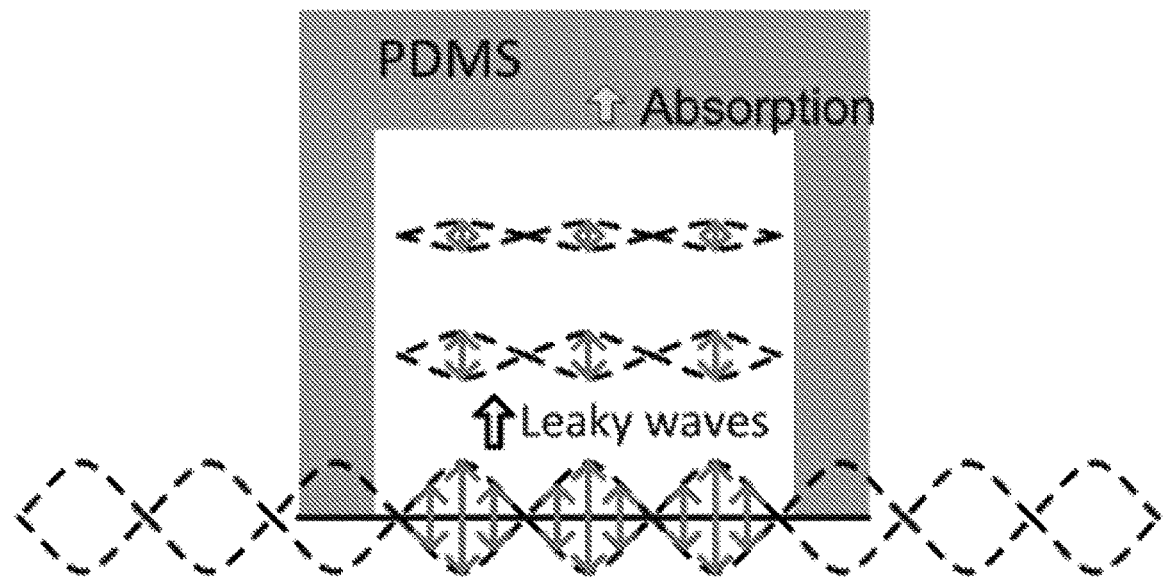
FIG. 4(A) is a schematic cross-sectional diagram of the illustrative prior art PDMS microfluidic channel.
Figure 4B:
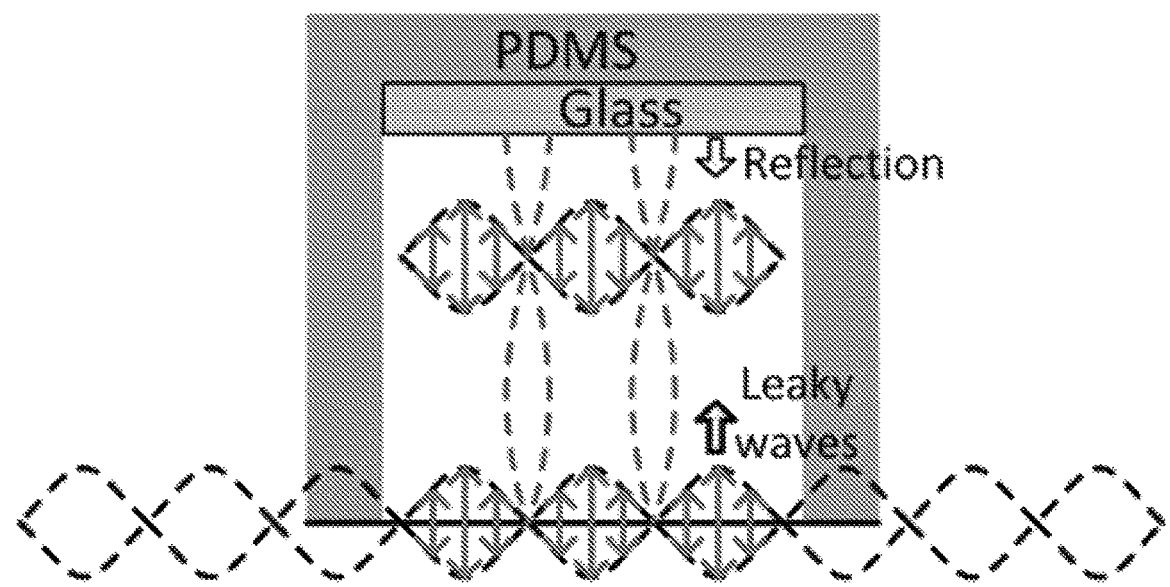
FIG. 4(B) is a schematic cross-sectional diagram of the illustrative hybrid PDMS-glass microfluidic channel according to aspects of the present disclosure.

With simultaneous reference now to FIG. 4(A), and FIG. 4(B), there is shown a schematic cross-sectional diagram of the illustrative prior art PDMS microfluidic channel (FIG. 4(A)) and a schematic cross-sectional diagram of the illustrative hybrid PDMS-glass microfluidic channel according to aspects of the present disclosure (FIG. 4(B)).

By cursory inspection of these figures, it is illustratively shown that the structure of FIG. 4(A) will absorb a considerable amount of acoustic energy thereby reducing the amount of energy available to reorient/sort particles flowing through the microfluidic channel. Conversely, the structure of FIG. 4(B)—by employing glass—or other suitably hard, acoustic reflective material—applies much more acoustic energy to the particles thereby enhancing the separation effect(s).

As will be readily appreciated and understood by those skilled in the art, glass has a much larger acoustic impedance (~12 MPa·s/m) than PDMS (0.98 MPa·s/m) and water (~1.49 MPa·s/m). Thus, whereas only 4% of the acoustic energy is reflected back to the channel in the PDMS channel used in our previous design shown illustrative in FIG. 4(A), the reflected acoustic energy is increased to 89% in the new hybrid PDMS-glass channel shown illustratively in FIG. 4(B).

As noted, to enhance the acoustic energy density within the microchannel and to improve the throughput of the acoustic separation device, we employ a PDMS-glass hybrid channel to form an acoustic enclosure. Within this hybrid enclosure, the horizontal displacement of the surface parallel to the piezoelectric substrate which generates the Rayleigh waves is cancelled, and only the vertical displacement component will propagate leaky acoustic waves into the fluid (FIG. 4(A)). The leaky waves travel in the fluidic domain and encounter the water-PDMS interface. The acoustic impedances of the water and PDMS are ~1.49 MPa·s/m and 0.98 MPa·s/m, respectively. The reflection coefficient $R_{water-PDMS}$ is calculated as:

$$R_{water-PDMS} = \left(\frac{Z_{PDMS} - Z_{water}}{Z_{PDMS} + Z_{water}}\right)^2 = 0.04$$

Only 4% of the acoustic energy is reflected back to the channel, while the vast majority is absorbed by the PDMS. Considering that the attenuation coefficient of PDMS is 3.3457 dB/MHz·cm, which is thousands of times higher than that of water (0.002 dB/MHz·cm), most of the acoustic energy transmitting into the PDMS is dissipated and wasted.

In order to reduce this energy loss, we embedded a thin glass layer (130 µm in thickness) at the top of the microchannel. Glass has a much larger acoustic impedance (~12 MPa·s/m) than PDMS and water. The reflection coefficients of the water-glass interface and the glass-PDMS interface are 0.61 and 0.72, respectively. Therefore, the reflected acoustic energy is increased to 89%. With the use of a hybrid PDMS-glass channel as a resonator, the acoustic energy that is enclosed within the fluidic domain is increased dramatically compared with the original PDMS channel.

Figure 4C:
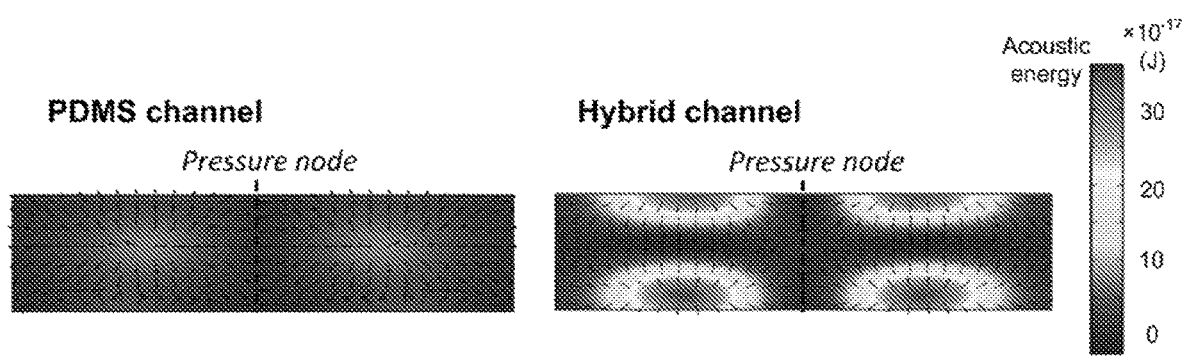
FIG. 4(C) are plots of a numerical simulation for the PDMS channel and Hybrid channel of acoustic energy density in the channels. The simulations illustrate that the hybrid channel exhibits a higher acoustic energy density because of the acoustic enclosure including the glass top surface.

FIG. 4(C) shows plots of a numerical simulation for the PDMS channel and Hybrid channel of acoustic energy density in the channels. The simulations illustrate that the hybrid channel exhibits a higher acoustic energy density because of the acoustic enclosure including the glass top surface. With the higher acoustic energy density, devices constructed in this manner according to aspects of the present disclosure generate larger acoustic radiation forces on particles as they flow through the microfluidic channel thereby enabling higher separation throughput.

Figure 4D:
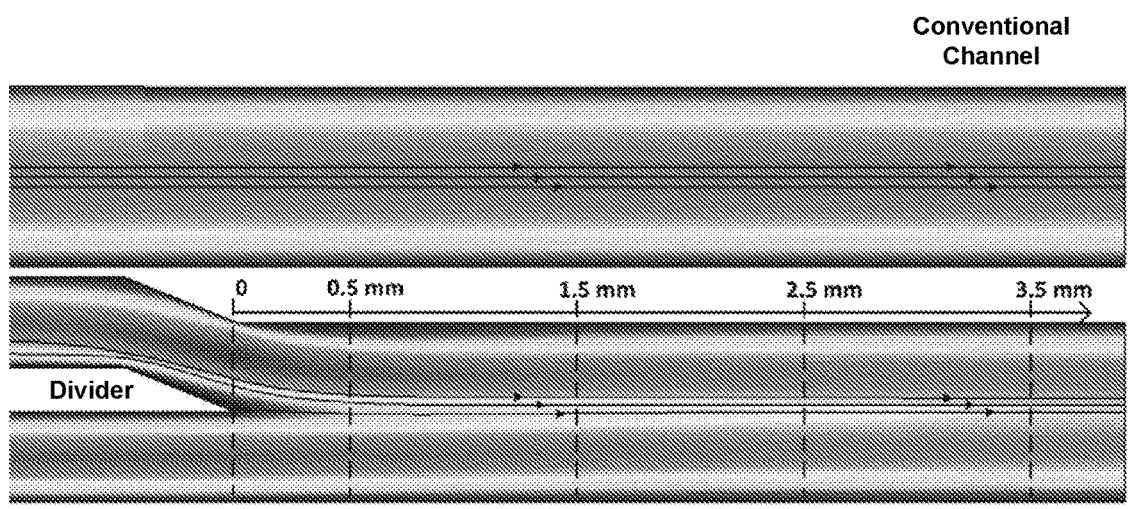
FIG. 4(D), FIG. 4(E), and FIG. 4(F) are plots of a numerical simulation for a modified channel with a divider and its effectiveness at increasing separation efficiency illustrating.
Figure 4E:
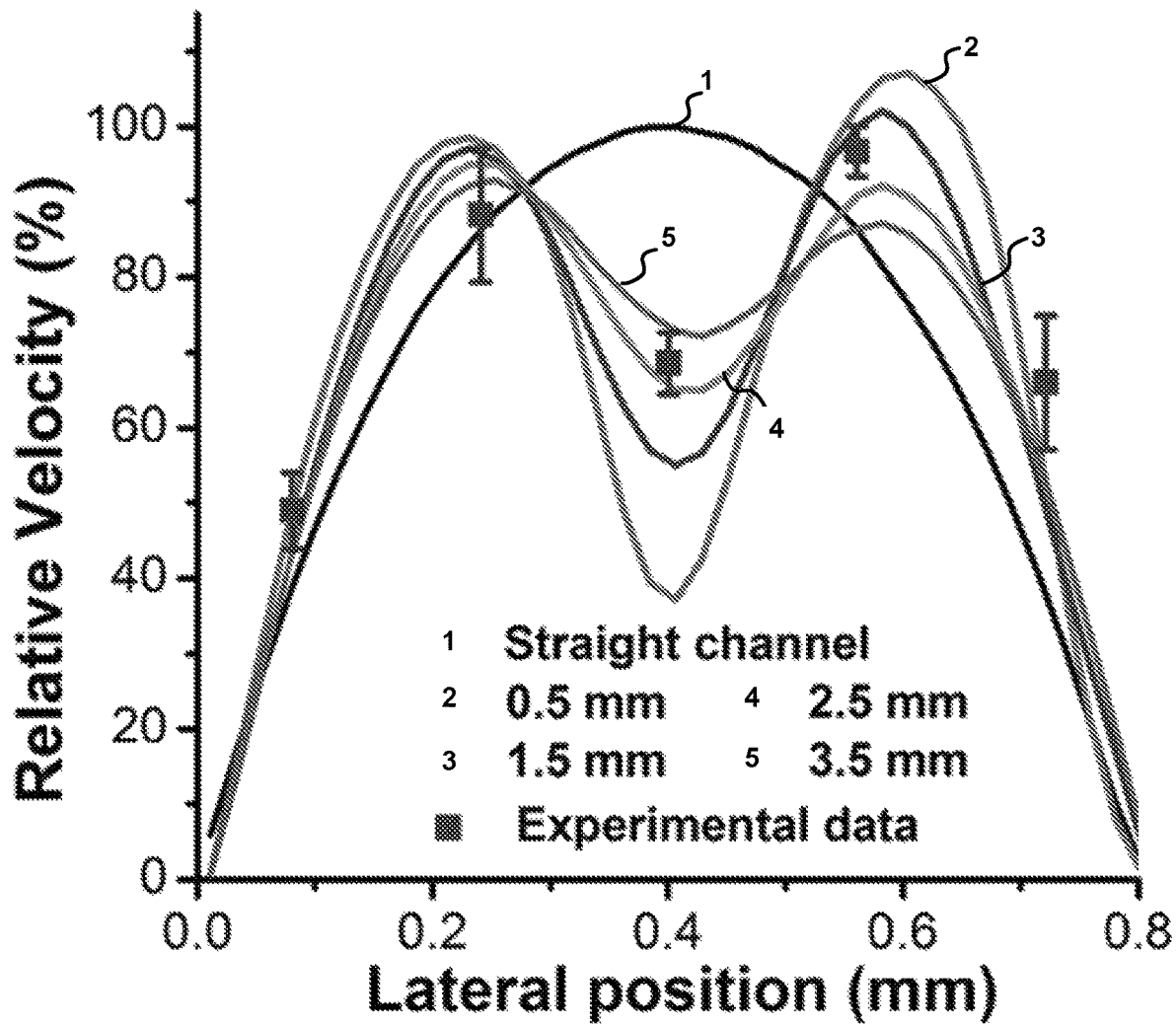
Figure 4F:
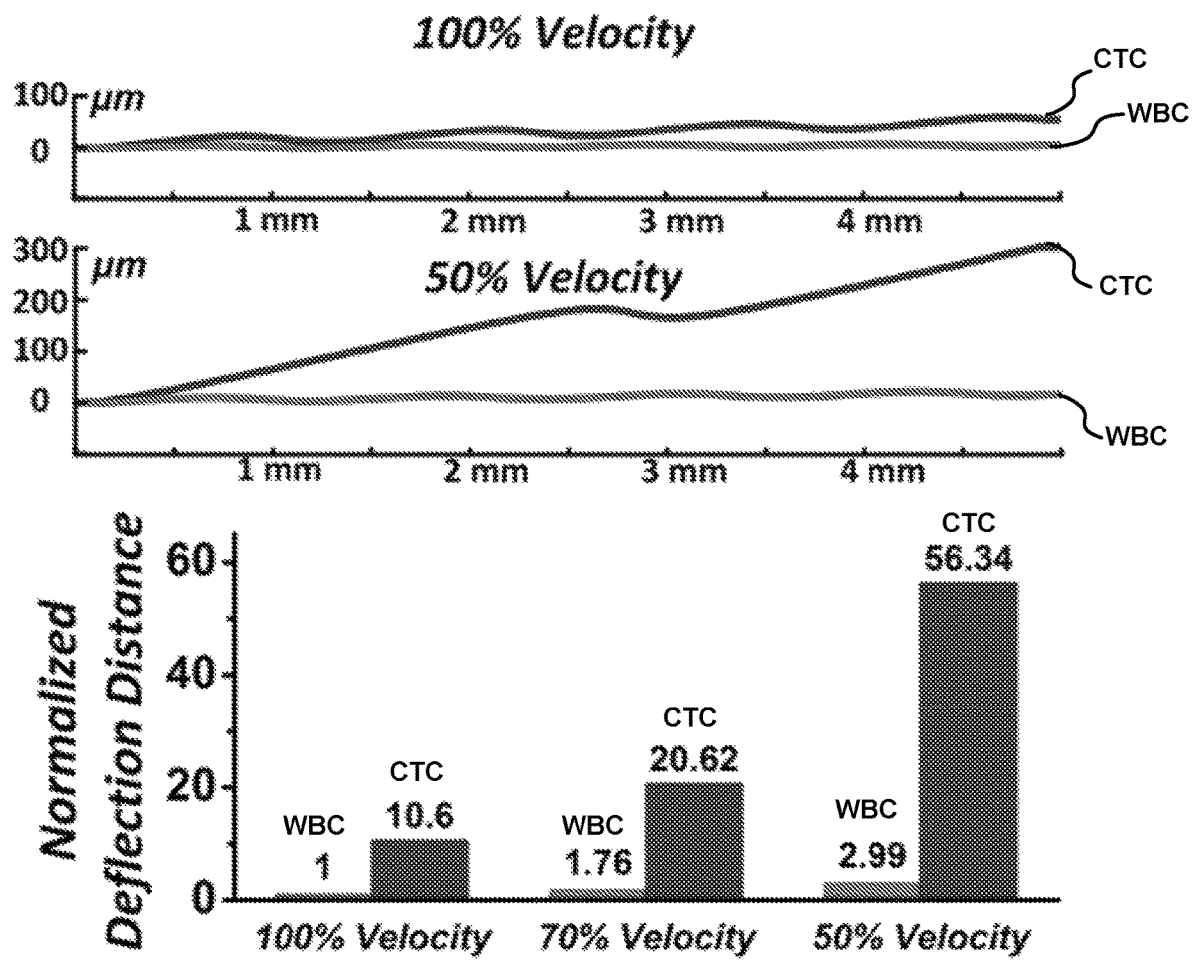

FIG. 4(D), FIG. 4(E), and FIG. 4(F) are plots of a numerical simulation for a modified channel with a divider and its effectiveness at increasing separation efficiency illustrating: FIG. 4(D) top view of the velocity distributions in the conventional channel (top) and modified channel with a divider (bottom) wherein arrows indicate positions of particles flowing in either channel with perimeter regions exhibiting low velocity while central regions exhibiting higher velocities; FIG. 4(E) velocity distribution curves across the channels showing that in the modified channel a low velocity region was created in the center after the PDMS divider and the velocity profiles in planes at 0.5, 1.5, 2.5, and 35 mm, with respect to the flow direction, after the PDMS divider are graphed; and FIG. 4(F) experimental data showing the lateral deflection displacements of particles (CTCs, WBCs) impacted by velocity—wherein a slower velocity increased the displacement;

In order to further improve the separation efficiency while maintaining high throughput, we modified the channel configuration by introducing a PDMS divider at the junction of the inlets (FIG. 2)).

FIG. 4(D) shows the ability of the PDMS divider to adjust fluid velocity profiles in the microchannel. For a simple straight channel, the velocity profile in the cross section maintains a parabolic distribution: at the channel walls, the velocity of the fluid is zero. The velocity increases towards the center of the channel and reaches a maximum at the center. In the prior art, the cell solution was infused from the central inlet so that the cells would be focused in the center of the channel (as indicated by the arrows), where the velocity is maximum. In designs according to aspects of the present disclosure, a PDMS divider is located in the center of the modified channel creating two additional boundary layers besides those from the channel walls; the downstream flow profile changes accordingly.

As a result, a shadow-like, low-velocity region forms and spans the acoustic field (FIG. 4(D)). In this case, cells are focused near the PDMS divider and their flow is retarded due to viscous forces. The cells continue traveling slowly as they enter the active acoustic region.

FIG. 4(E) shows the velocity distribution of a straight channel (parabolic curve) compared against the velocity distribution at various positions along the modified channel. At a distance of 0.5 mm after the channel convergence, the fluid velocity is reduced by approximately 60% in the center as compared to that of the straight channel. Even 3.5 mm away from the PDMS divider, the velocity profile is still reduced by more than 20%. The simulation is supported by experimental data, which indicate a significant drop in velocity at the center of the channel. The experimental results were obtained by recording particle trajectories and calculating the velocities of 50 individual particles distributed throughout each region.

The velocity shadow successfully decreased the speed of the cells as they entered the acoustic field zone, enabling more time for the acoustic radiation force to differentiate CTCs from WBCs. The resulting lateral displacement induced by acoustic field is thus enhanced when compared to the straight channel design.

FIG. 4(F) shows a numerical simulation of cell deflection as a function of flow velocity. The trajectories of the CTCs and WBCs are simulated under the conditions of 100% and 50% of the maximum velocity in a straight channel. From the trajectories, the decrease in velocity leads to a larger lateral shift and as such, CTCs can be separated from WBCs more efficiently. We then calculated the lateral deflection distance of the CTCs and WBCs under different velocities. For WBCs the distance increases 1.76 times and 2.99 times, respectively, when the velocities are 70% and 50%, respectively, when compared against the situation that the velocity of cells equates to the maximum velocity in a straight channel. As for CTCs at 50% velocity, the shift is 5.3 times greater than at 100% velocity. The difference in the lateral deflection between CTCs and WBCs, which increases from 10 times to 18.8 times, is noteworthy. Thus, by implementing this divider design, we have improved the overall lateral displacement of CTCs and markedly enhanced the separation efficiency.

At this point we note that illustrative devices and structures have been fabricated using Y+128° X-propagation lithium niobate (LiNbO$_3$) as piezoelectric substrates. The IDT design was patterned by photolithography using a MA/BA6 mask aligner (SUSS MicroTec., Germany). After that, 50 Å of Cr was deposited as an adhesive layer, followed by a 500 Å gold layer for electrode fabrication. The deposition was conducted with an e-beam evaporator (Semicore Corp, USA). Finally, the metal layer was removed with photoresist and IDTs were formed by a lift-off process.

Figure 5:
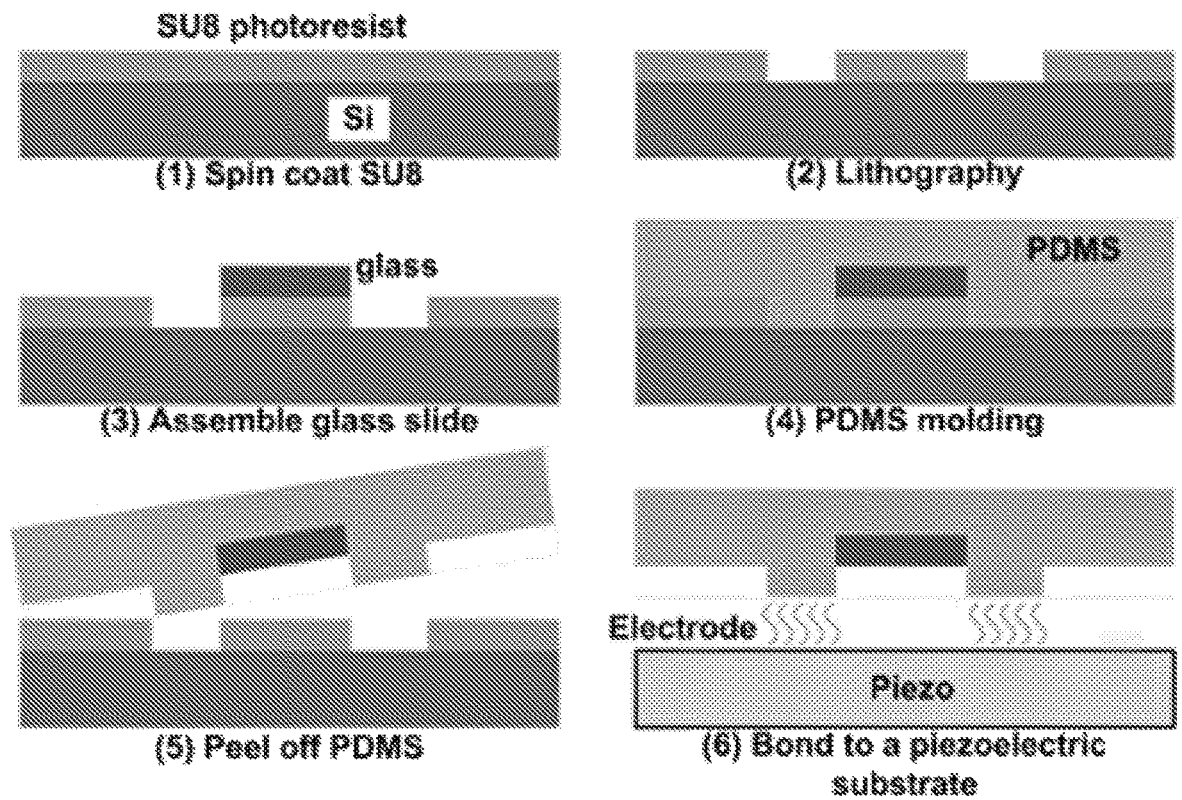
FIG. 5 is a schematic diagram of an illustrative sequence of processing steps that may be employed in fabricating hybrid microfluidic channel structures according to aspects of the present disclosure.

The PDMS/glass hybrid channel was fabricated by a standard soft lithography process, as shown in FIG. 5. A thin layer of SU8 100 photoresist (MicroChem, USA) was spin-coated and patterned by UV exposure on a silicon wafer. A glass slide was placed on the SU8 mold at the designed position where standing acoustic filed was formed. The glass slide was made from micro cover glass (VWR, USA), and was cut to 800 µm×5 mm by laser cutting. Sylgard 184 Silicone Elastomer Curing Agent and Base (Dow Corning, USA) was mixed at 1:10 and poured on the mold. After setting at room temperature overnight, the PDMS channel was peeled from the mold and bonded to the LiNbO$_3$ substrate. Before bonding, the surface of the LiNbO$_3$ substrate and the PDMS channel was treated with oxygen plasma.

To evaluate our structures, we successfully separated CTCs and WBCs. Operationally, the high-throughput acoustic separation device according to aspects of the present disclosure was placed on a Peltier cooler (TEC1-12730, Hebei I.T., China) which served as a heat sink. The voltage for the cooler was ~2V. The device and cooler were placed on the stage of an upright microscope (BX51WI, Olympus, Japan) during the separation experiment. The fluid flows, including sheath fluid and sample fluid, were controlled by individual syringe pumps (neMESYS, cetoni GmbH, Germany). Before each experiment, ethanol was flushed through the whole microfluidic device to remove air bubbles from the channel, followed by PBS washing for 3 min. Then the channel was filled with 1% bovine serum albumin (Sigma-Aldrich, USA) solution and left for 5 min to coat the channel surface. The sample mixture was then introduced to the device at a flow rate of 125 μL/min. The flow rates for two sheath fluids were 110 μL/min and 220 μL/min. Cells from the device outlets were collected either in a 35×10 mm Petri dish (Corning) or 1.7 mL Eppendorf centrifuge tubes. The acoustic wave was excited by applying a radio frequency (RF) signal to the IDTs on the piezoelectric substrate. The RF signal was generated by a function generator (E4422B; Agilent, USA) and an amplifier (25A100A; Amplifier Research, USA). The frequency was set at 19.9 MHz, and the power inputs ranged from 32 to 35 dBm.

As noted above, systems, methods, and structures according to aspects of the present disclosure have proven to improve continuous separation throughput of up to 7.5 mL/hr. Even operating at this improved throughput, separation efficiency was evaluated by separating cancer cells from white blood cells in a clinical setting. Advantageously, we successfully separated CTCs from blood samples from metastatic prostate cancer and characterizing the phenotypic heterogeneity of prostate CTS.

More specifically, to test the effectiveness of the Hybrid PDMS-glass resonator and divider in improving separation throughput and accuracy, we used the separation devices to isolate PC-3, LnCaP, HeLa, and MCF-7 cancer cells, which represent a range of hormone-sensitive prostate cancer cells, castration-resistant prostate cancer cells, cervical cancer cultured cell lines, and breast cancer cultured cell lines, respectively.

WBCs were collected from 1 mL of blood from healthy volunteers and then re-suspended with cancer cells stained with Calcein-AM in PBS. In order to improve visualization of the separation process, a large number of cancer cells are mixed with this suspension. The ratio of cancer cells to WBCs varied from 1:5 to 1:10. Cell separation at the outlet region was recorded under fluorescent microscopes.

Cells were focused in the center of the channel through the operation of the separator structure. The flow rate of the cell stream was 7.5 mL/h, and the flow rates of the two sheath flows were 6.6 mL/h and 13.2 mL/h, respectively. When the acoustic field was not activated, cells were not deflected and all flowed toward the waste (upper) outlet. Once the acoustic field was activated, there was a clear separation between cancer cells and healthy WBCs. Cancer cells, which are stained with green fluorescence, were deflected by the acoustic field and directed toward the collection outlet (lower), whereas the majority of WBCs remained in the waste outlet. This experimentally demonstrates that our acoustic separation platform can separate cancer cells from WBCs at a flow rate of 7.5 mL/h.

Next, we performed an isolation process that modeled rare cancer cells in whole blood. The rare cell population was simulated by incorporating 50 to 1,000 Calcein-AM-stained cancer cells into 1 mL of WBCs. The concentration of WBCs ranged from 3 to 6 million cells per mL. This mixture was processed through the acoustic separation device at a flow rate of 7.5 mL/h. Cells were gathered from both the collection and waste outlets. The fluorescent cancer cells were counted at both outlets, and the recovery rate was calculated by dividing the number of cancer cells in the collection outlet by the total number cancer cells from both outlets. An average recovery rate greater than 86% is obtained for all these samples.

To verify if our new separation device preserves cell integrity, we conducted long-term cell culture of PC-3 and LnCaP cells, following acoustic separation. The flow rate and input power were the same as those used in the cell separation experiments above. Cells collected from the collection outlet were cultured in an incubator and were monitored. The morphology of the separated cancer cells appeared to be consistent with those known in the literature. They started to attach to the Petri dish after 12 h and proliferated every 2 days, suggesting that the cells recovered after sorting and proliferated at a rate similar to that before sorting.

After demonstrating cancer cell separation with blood samples that contained pre-determined proportions of cancer cells from cultures, we performed CTC separation using blood samples that were collected from patients with prostate cancer. Men with castration-resistant metastatic prostate cancer and widespread bone metastases were enrolled as part of an IRB-approved clinical protocol at Duke University under informed consent, and blood samples were collected for CTC isolation. All men were receiving radium-223 therapy as part of their standard therapy, and all had received prior hormonal therapies for metastatic prostate cancer. Immunostaining of cytokeratin 8, 18(CK8, 18) and pan-leukocyte marker CD45 as well as nucleus staining of DAPI were used to identify the cells. CTCs were identified as CK8,18+/CD45−/DAPI+; DAPI− was regarded as debris or dust; cells were otherwise identified as WBCs.

Based on immunostaining criteria, we have identified CTCs from five clinical blood samples, with counts ranging from 0.93 to 400 CTCs per mL. We also examined the expression of the PSMA, which is a transmembrane protein that has considerable overexpression on most prostate cancer cells, and thus is used as a diagnostic imaging target and has emerged as a potential therapeutic target. We examined PSMA expression in CTCs. It is notable that although the majority of prostate cancer CTCs had PSMA overexpression, a fraction of the CTCs expressed relatively low levels of PSMA. Loss of PSMA positivity in the CTCs from prostate cancer patients could be a reflection of tumor heterogeneity and suppression of androgen receptor activity during castration-resistant progression. This result also indicates that PSMA-targeted imaging and directed therapies could miss some of the tumor cells and therefore be ineffective.

We also characterized the size distribution of CTCs and WBCs. The diameters of 70 CTCs and 64 WBCs were measured and are plotted in FIG. 6B. The diameter of CTCs has a median diameter of 16.5 μm with a 95% confidence interval at 0.61 μm. Furthermore, 50% of the CTCs ranged from 14.5 to 18 μm. The WBCs' diameters were 11.8±0.54 μm; 50% of the WBCs were within 10.5-14 μm diameter.

The size distribution of WBCs and CTCs present P values less than 0.0001. However, it is noteworthy that the size distributions of CTCs and WBCs overlapped.

Additionally, it is notable that while most of the CTCs isolated using the acoustic separation device were single cells, we also identified several CTCs that were present as clusters of 2-3 cells. Although clustered CTCs were even rarer when compared to single CTCs, CTC clusters may be of greater relevance than single CTCs for improving our understating of the mechanisms of metastasis. Further studies on clustered CTCs could be valuable to identifying CTC subgroups and CTC cells, and may reveal important information about the metastatic process.

Lastly, the immunostaining identified some cells with both cytokeratin and leukocyte markers, namely CK8,18+ and CD45+. Although these "double-positive" cells are typically excluded from CTC enumeration, they might be inherently related to CTCs. In addition, these double-positive cells are observed rarely in healthy donors' blood samples. The identity of these double-positive cells is currently not well understood. These CTCs may be "disguised" upon ingestion of leukocyte-derived proteins, while some monocytes may be coated with tumor-derived markers. To address this situation, further studies such as using other specific markers need to be performed with our acoustic separation platform. Our study shows that the double-positive cells are present in two categories: clusters with other CTCs and as individual cells. The presence of cell clusters with CTCs and dual-positive cells suggests that cell-to-cell interactions are a possible mechanism for the formation of these dual-positive cells.

As a further illustrative example of systems, methods, and structures according to aspects of the present disclosure, we have shown an integrated, on-chip structure capable of isolating exomes directly from undiluted whole blood samples in a continuous, automated manner.

As will be readily appreciated by those skilled in the art, when dealing with a complex fluid such as undiluted blood, the wide size range of blood-borne components (10 nm~20 μm) presents significant challenges for separation techniques. To overcome this technical barrier, we describe a two-module separator structure—that may advantageously be integrated onto a single substrate—that can sequentially separate blood cells from EVs, and then further differentiate the subtypes of EVs.

Figure 6:
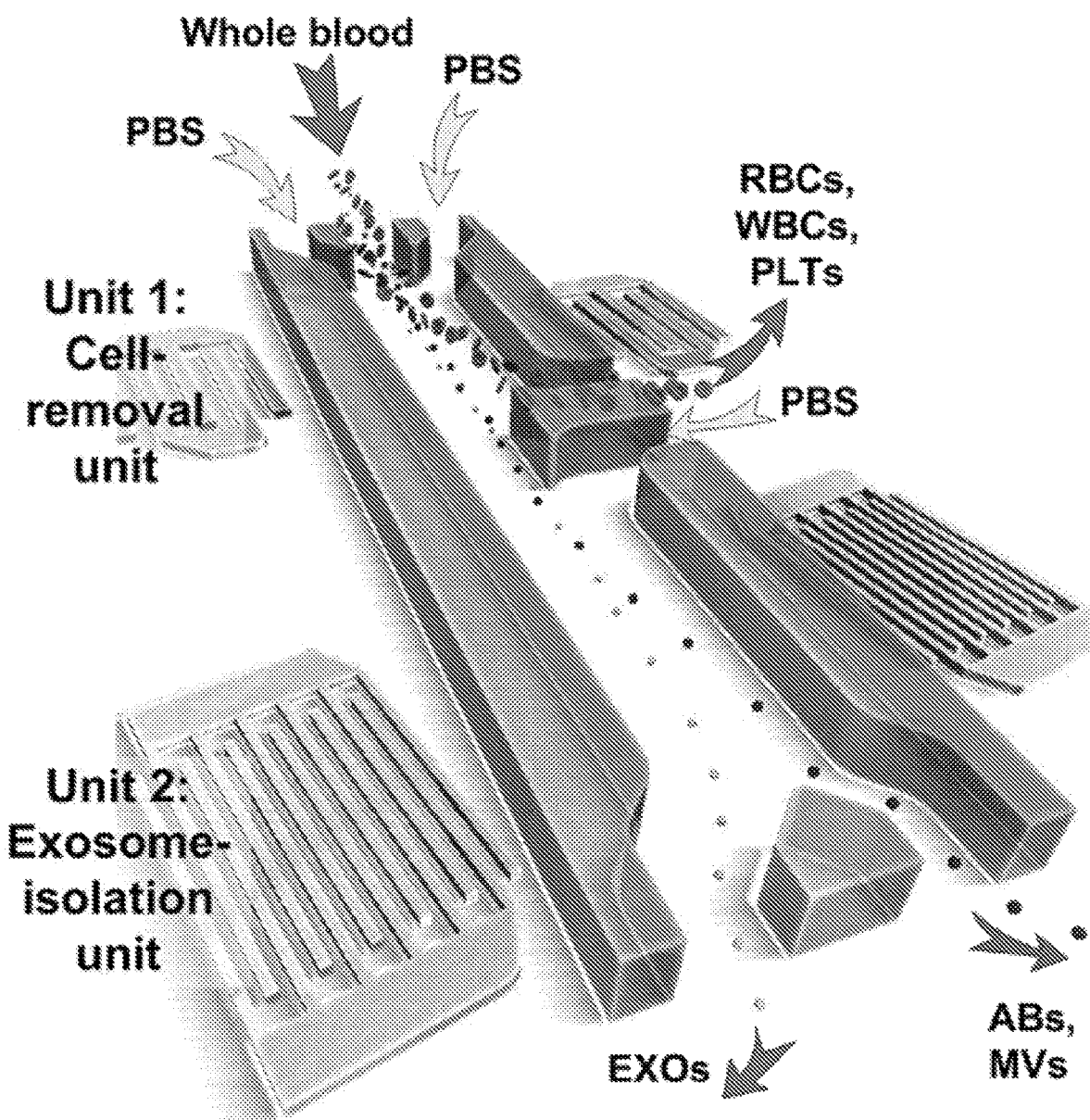
FIG. 6 is a perspective schematic diagram of the illustrative integrated acoustofluidic separation structure that may advantageously be employed to separate exosomes including a cell-removal unit and an exosome-isolation unit cascaded on a single chip according to aspects of the present disclosure.

Turning now to FIG. 6, there is shown a perspective schematic diagram of the illustrative integrated acoustofluidic separation structure that may advantageously be employed to separate exosomes including a cell-removal unit and an exosome-isolation unit cascaded on a single chip according to aspects of the present disclosure. As illustratively shown in that figure, the acoustofluidic separation structure includes a cell-removal module and an exosome-isolation module. The cell-removal module is designed to first fractionate blood components larger than 1 μm, including red blood cells (RBCs), white blood cells (WBCs), and platelets. This provides cell-free plasma for the downstream unit, namely, the exosome-isolation module, which may be configured (optimized) to separate nanoscale bioparticles. By using a higher frequency (~40 MHz) than those used in our previous acoustofluidic devices, the exosome-isolation module enables the discrimination of submicron particles, such that subgroups of EVs with larger size (including microvesicles (MVs) and apoptotic bodies (ABs)) are separated from EVs, thereby preserving the exosomes. With two sequential separations in one integrated device, nano-sized exosomes are promptly isolated from undiluted human blood.

With continued reference to that FIG. 6, it may be further observed that the device illustrated therein includes an elongated channel structure having three input ports at one end, a pair of outlet port at an opposite end, and an intermediate (waste) input/output port formed on one side. Shown further is a cell removal unit/region including a pair of IDTs and a "downstream", exome-isolation/separation unit/region including an additional pair of IDTs. Note that the intermediate (waste) input/output port formed in a side wall of the channel is positioned between the cell-removal region and the exome-isolation region.

Operationally, whole blood is introduced at the central input port while two phosphate-buffered saline (PBS) sheath flows are introduced into the two ports on either side of the central port. Particles comprising the whole blood (RBCs, WBCs, PLTs, EXOs, Abs, MVs, etc) are redirected during flow through the channel by tilted-angle standing acoustic field generated by the IDTs comprising the cell removal unit and—later in flow—the exome-isolation unit. Note that as the particles undergo the effects of the cell removal unit, particular large cells including the RBCs, WBCs, and PLTs are redirected to the side-formed waste port. Additional PBS is injected into an input portion of the waste port and particles remaining in the flow are further redirected through the effects of the exosome-isolation unit which further separates the EXOs from the ABs and MVs, which in turn are directed to separate output ports as shown. As discussed previously, the periodic distribution of pressure nodes and antinodes generates an acoustic radiation force to push large particles towards node planes.

Figure 7:
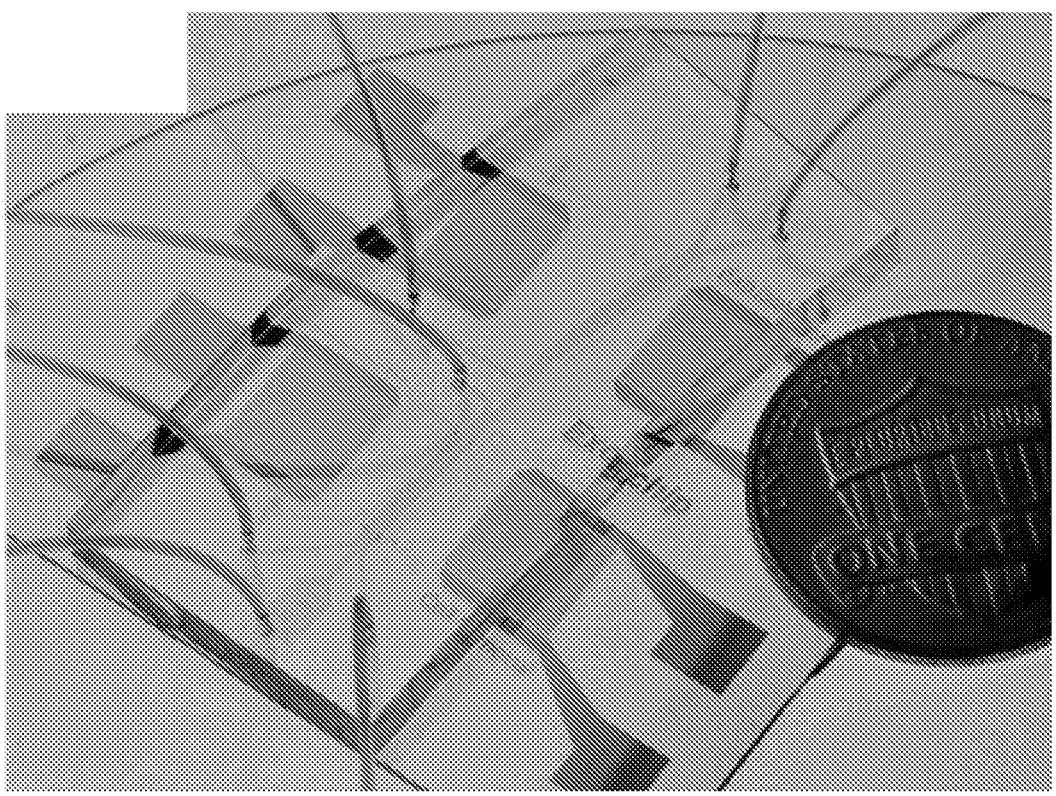
FIG. 7 is a photoillustration of an illustrative, integrated acoustofluidic structure including multiple separation structures such as that shown in FIG. 6 according to aspects of the present disclosure.

FIG. 7 is a photoillustration of an illustrative, integrated acoustofluidic structure including multiple separation structures such as that shown in FIG. 6 according to aspects of the present disclosure. The integrated acoustofluidic separation device shown therein (FIG. 7) illustratively includes a lithium niobate (LiNbO$_3$) substrate, two pairs of IDTs, and a polydimethylsiloxane (PDMS) microchannel. The two IDTs are deposited on the LiNbO$_3$ substrate using photolithography and liftoff processes, and their driving frequencies are designed as ~20 MHz and ~40 MHz, respectively. The PDMS microchannel is bonded onto the LiNbO$_3$ substrate in between the IDTs. The channel includes the following ports: a sample inlet for whole blood, three inlets for buffer solution as sheath flows, an outlet for blood cells (Waste), an outlet for subgroups of EVs other than exosomes, and an outlet for purified exosomes. A pre-filtration unit, in which PDMS pillar arrays were constructed, is placed in the blood sample inlet to prevent the blood cells from aggregating. The microchannel is aligned to form specific angles with respect to IDTs. Based on our numerical and experimental investigations, the optimal angles between the channel and IDTs are 5° and 15° for the cell-removal module and the exosome-isolation module, respectively.

Figure 8:
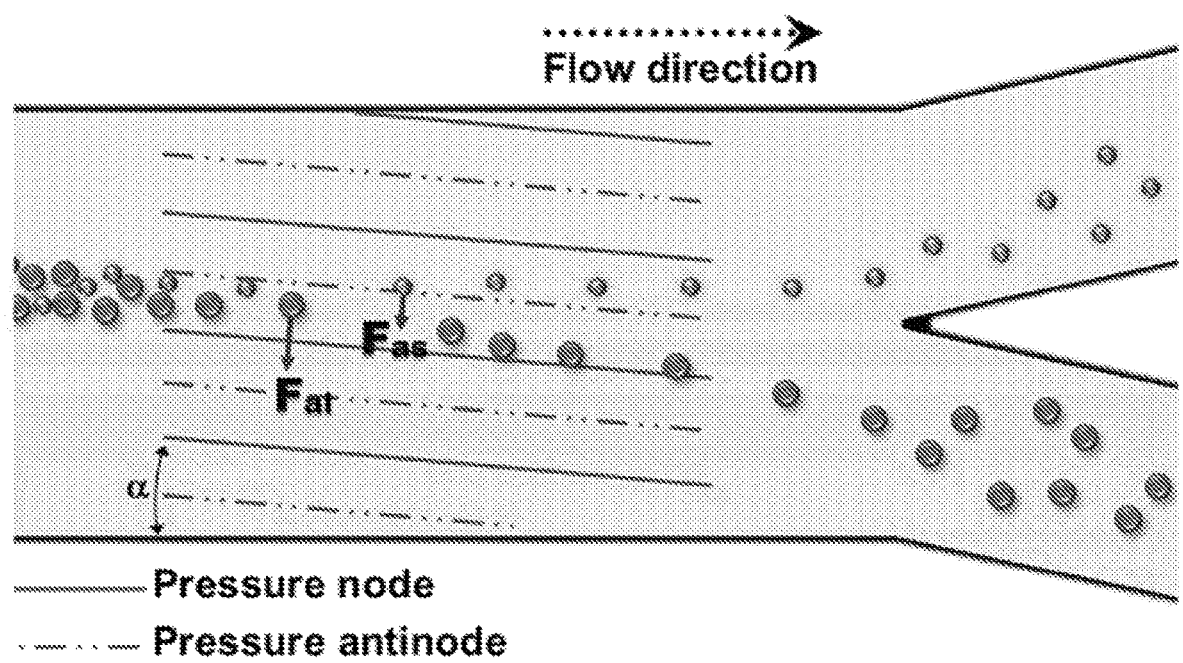
FIG. 8 is a schematic diagram of a top view of an acoustofluidic structure illustrating size-based separation occurring in each separation structure (module) due to lateral deflection induced by a tilted-angle standing acoustic field wherein periodic distribution of pressure nodes and antinodes generates an acoustic radiation force to push large particles towards node planes according to aspects of the present disclosure.

FIG. 8 is a schematic diagram of a top view of an acoustofluidic structure illustrating size-based separation occurring in each separation structure (module) due to lateral deflection induced by a tilted-angle standing acoustic field wherein periodic distribution of pressure nodes and antinodes generates an acoustic radiation force to push large particles towards node planes according to aspects of the present disclosure.

As illustrated in this figure, the separation mechanism of larger particles and smaller particles due to the deflection caused by acoustic pressure nodes tilted with respect to the channel orientation. Particles are subjected to an acoustic radiation force ($F_r$) generated by the SAW field, as described by equation (1) and (2):

$$F_r = -\left(\frac{\pi p_0^2 V_p \beta_f}{2\lambda}\right)\phi(\beta, \rho)\sin(2kx) \quad [1]$$

$$\phi(\beta, \rho) = \frac{5\rho_p - 2\rho_f}{2\rho_p + \rho_f} - \frac{\beta_p}{\beta_f} \quad [2]$$

In these equations, $p_0$, $V_p$, $\lambda$, $k$, $x$, $\rho_p$, $\rho_f$, $\beta_p$, and $\beta_f$ are acoustic pressure, volume of the particle, wavelength, wave number, distance from a pressure node, density of the particle, density of the fluid, compressibility of the particle, and compressibility of the fluid, respectively. Equation (2) is the expression for the acoustic contrast factor $\Phi$, which determines whether the particle moves towards pressure nodes or antinodes in the SAW field. For cells and vesicles, the acoustic contrast factor is positive, which means that they will move towards pressure nodes.

As particles move toward the pressure nodes because of the acoustic radiation force, their movement is also impeded by the Stokes drag force ($F_d$):

$$F_d = -6\pi\eta R_p(u_p - u_f) \quad [3]$$

where $\eta$, $R_p$, $u_p$, and $u_f$ are the viscosity of the fluid, radius of the particle, velocity of the particle, and velocity of the fluid, respectively.

Drag force is proportional to the radius of the particles or cells and the acoustic radiation force is proportional to the volume. Thus, the acoustic radiation force dominates over the drag force for larger particles, which causes the particle stream to translate towards the tilted nodes. Conversely, the drag force cancels a significant part of acoustic radiation force out for smaller particles, resulting in little lateral displacement. Depending on their differences in size, particles are therefore directed to different outlets. Simply by adjusting the input power, our acoustofluidic-based separation strategy is capable of increasing or decreasing the cutoff diameter. This feature gives our device the flexibility to be used for a wide variety of applications.

To obtain the optimal parameters for the cell-removal module, we first examined whether our device was able to separate a mixture of synthetic particles of two different sizes. We used polystyrene particles of 970 nm mimicking a subset of EVs present in human blood, and 5.84 µm particles that mimicked RBCs and WBCs. Polystyrene particles of 970 nm were conjugated with a green fluorophore, facilitating real-time tracking of their trajectory during the course of separation.

We forced the particle mixture into a narrow, straight sample stream by introducing two phosphate-buffered saline (PBS) sheath flows through the two adjacent inlets. Using a driving frequency of 19.573 MHz under an input power of 22 VPP, we were able to direct 5.84 µm particles toward the waste outlet, whereas 970 nm particles remained in the sample stream and exited through the collection outlet. This result suggests that, upon exposure to a standing SAW field, particles of diameter 5.84 were successfully separated from particles of 970 nm diameter. Given that the exosomes present in human blood are known to be in the range of 30-150 nm, we used polystyrene particles of 110 nm to mimic blood-borne exosomes. Using the same cell-removal module, we further found that we could separate polystyrene particles of 110 nm from particles of 5 µm with a recovery rate of over 99% (Figure S1 in the Supporting Information). These results demonstrate the capability of our acoustofluidic approach for isolating nanoparticles from a mixture consisting of both nanoparticles and microparticles.

Based on the optimized conditions obtained from the pilot experiments (separating a mixture of polystyrene particles), we proceeded to test our cell-removal module using undiluted whole blood samples treated with anticoagulant agent EDTA. Since blood cells have lower acoustic contrast than polystyrene particles, we increased the input power to 40 Vpp. To match the acoustic impedance of whole blood, 5% dextrose solution in PBS was used as sheath fluid. When the taSSAW field was off, the whole blood sample flowed into the top outlet. Once the taSSAW was activated, blood components such as blood cells and platelets changed their flow route and were delivered to the waste outlet.

Samples collected from the two outlets were measured through nanoparticle tracking analysis (NTA) and dynamic light scattering (DLS), respectively. The sample collected at the waste outlet has a visible peak at ~5 µm, which refers to as RBCs, while the sample collected at the collection outlet, the isolated EVs sample, contained no particles larger than 1 µm, thus suggesting that only bioparticles smaller than 1 µm, such as EVs, were isolated. To further characterize isolated EVs, we employed a scanning electron microscope (SEM) and western blotting. The SEM showed that the diameters of isolated EVs ranged from 50-300 nm. Moreover, western blotting shows that samples from the waste outlet which presumably contained blood cells and platelets were positive for Integrin 131 (platelet marker) and Glycophrin A (a representative marker of RBCs). In contrast, our isolated EVs were immune-positive for CD63, the canonical EV markers, and negative for platelet and RBC markers (FIG. 3d). Collectively, these results demonstrate that our acoustofluidic-based cell-removal module is capable of separating EVs directly from undiluted human blood samples.

To examine whether our exosome-isolation module could separate EV subgroups such as microvesicles and exosomes, we input a mixture of purified exosomes and microvesicles derived from primary human trophoblasts (PHT). PHT-derived microvesicles and exosomes were purified from a PHT-conditioned medium and characterized via known methods. We identified an optimized driving frequency of 39.41 MHz based on our pilot experiments using a nanoparticle mixture of 110 nm and 340 nm. Then, we set the sample flow rate and sheath flow rate as 4 and 8 µL/min, respectively. With the standing SAW field switched on under an input power of 45 Vpp, larger bioparticles were deflected and directed to the waste outlet. We then conducted NTA on the isolated samples from both outlets as well as on the original mixture of the same volume. The original mixture of purified microvesicles and exosomes had a board size distribution from ~50 nm to 600 nm; specifically, there was a single peak at 122 nm, which was referred to be exosomes, whereas other peaks appeared between 170 nm and 300 nm represented the broader distribution of microvesicles compared to exosomes. Additionally, the concentration distribution curve reached a valley at 140 nm, which was therefore chosen as the cut-off size for separation. The sample at the collection outlet exhibited only one peak between ~50 nm to 100 nm, and the peak position presented a modest shift from 122 nm to 99 nm, which may be caused by resolution limits of NTA when testing highly heterogeneous samples. The sample collected from the waste outlet, by contrast, exhibited several peaks larger than 170 nm along with very few components that were less than 100 nm. These results demonstrate that our acoustofluidic device is able to separate two distinct EVs from each other, i.e., PHT-derived microvesicles and exosomes.

We further quantified the concentrations of samples including an input mixture of trophoblastic microvesicles and exosomes, isolated microvesicles, and isolated exosomes, respectively. Given that the final volume of each outlet is 1.5-fold of the input sample volume because of PBS dilution effect during the course of separation, we corrected the particle concentrations measured from NTA by dividing by this coefficient (1.5). As such, we calculated that the original mixture contained, per microliter, $1.03 \times 10^8$ vesicles that were smaller than 140 nm (<140 nm) and $3.34 \times 10^8$ vesicles that were larger than 140 nm (>140 nm). The concentrations of particles collected from the exosome outlets were $8.42 \times 10^7$ (<140 nm) and $1.4 \times 10^6$ (>140 nm), respectively. The concentrations of particles collected from the microvesicle outlets were $1.8 \times 10^7$ (<140 nm) and $3.35 \times 10^8$ particles (>140 nm). The total numbers of vesicles before and after separation were $4.37 \times 10^8$ and $4.386 \times 10^8$, respectively. Moreover, the percentages of small particles and larger particles were comparable before (23.6%) and after separation (23.3%), suggesting that the acoustofluidic separation technique has a high yield and does not lose much samples during the separation process. Overall, the acoustofluidic-based exosome-isolation device shows excellent performance in terms of separating vesicle samples based on size difference; a purity of 98.4% was achieved for the particles smaller than 140 nm collected from the exosome outlet, and 82.4% of the small particles were directed to the exosome outlet. We also used TEM to characterize the morphology of the isolated exosomes. The mean size of isolated vesicles was around 100 nm, which is consistent with the NTA results.

Following testing and optimizing the individual modules, we integrated the cell-removal module and exosome-isolation module into a single acoustofluidic chip. We used undiluted human blood from healthy donors for EV isolation. The flow rates of each inlet were set to 4 µl/min for the blood sample, 4 µl/min and 12 µl/min for sheath flows in the cell-removal unit, and 10 µl/min for sheath flow in the exosome-isolation unit. The driving frequency and voltage of the input RF signal for the integrated device were the same as those used for individual units. When the acoustic field was off, the blood stream was focused in the middle of channel and is directed into the outlet F. When the RF signal was on for both modules, blood components were separated toward different outlets. The vast majority of blood cells and platelets were deflected to the outlet D, here called the cell-waste outlet, after passing through the cell-removal module. Subsequently, the exosome-isolation module, once activated, directs the apoptotic bodies, microvesicles, and the remaining part of cells to the outlet G, referred to as the vesicle-waste outlet, thereby isolating exosomes from whole blood samples.

Upon collecting samples from the exosome and vesicle waste outlets, we first characterized the cell-removal efficiency. The isolated exosome, vesicle waste, and unprocessed whole blood samples were added into 1.5 ml centrifuge tubes and spun down at 3,000 rpm for 10 minutes. The volume of cells in whole blood sample is nearly half of the total volume, which was the typical case for human blood. In contrast to the whole blood sample, there were very few blood cells remaining in the isolated exosome sample and the vesicle waste. We further quantified the number of blood cells in the exosome sample by using a hemocytometer. The concentration of cells was $2.08 \times 10^4$ cells per milliliter in the sample collected from the exosome outlet, while the RBC count reference ranged from 4.7 to $6.1 \times 10^{10}$ cells per milliliter, yielding a cell removal rate over 99.999%. We then tested the size distribution of isolated exosome samples through NTA. We also tested a plasma sample, which was obtained from the same whole blood sample, as a control group, since the cells in blood could impede NTA.

After separation, the sample collected from the exosome outlet showed a clear, narrow peak at around 100 nm, which corresponded to exosomes, while the control group displayed a flat, disperse curve covering a broad range from ~50 nm to 1 µm. The NTA results demonstrate that the acoustofluidic-based separation device differentiated subgroups of EVs based on size, and thereby isolated exosomes from the mixture.

At this point, while we have presented this disclosure using some specific examples, those skilled in the art will recognize that our teachings are not so limited. Accordingly, this disclosure should be only limited by the scope of the claims attached hereto.

The invention claimed is:

1. An acoustofluidic separation device comprising: a substrate having formed thereon:
    an elongated channel disposed thereon, said channel including a plurality of inlet ports at one end, a pair of outlet ports at an opposite end, and a waste input port and a waste output port at a location intermediate to the inlet ports and the outlet ports;
    a cell removal unit positioned between the inlet ports and the waste input port and the waste output port;
    an exosome isolation unit positioned between the waste input port and the waste output port and the outlet ports.

2. The separation device of claim 1 wherein the cell removal unit further comprises at least one ultrasonic transducer configured to generate an acoustic standing wave in a portion of the channel intermediate to the inlet ports and the waste input port and the waste output port.

3. The separation device of claim 1 wherein the cell removal unit further comprises at least one ultrasonic transducer configured to generate an acoustic standing wave in a portion of the channel intermediate to the waste input port and the waste output port and the outlet ports.

4. The separation device of claim 3 further comprising a pair of sheath flow inlets positioned on either side of the inlet ports.

5. The separation device of claim 4 further comprising a second outlet positioned at the opposite end of the channel adjacent to the outlet ports.

6. The separation device of claim 5 wherein the at least one ultrasonic transducer are configured to generate tilted angle standing surface acoustic waves (taSSAW) that produce pressure nodes within the channel.

7. The separation device of claim 6 wherein one of the outlet ports at the end of the channel is another waste port.

* * * * *